US012578326B2

(12) United States Patent
Rodriguez et al.

(10) Patent No.: US 12,578,326 B2
(45) Date of Patent: Mar. 17, 2026

(54) METHODS AND COMPOSITIONS FOR IDENTIFYING A SURVIVABILITY INDEX FOR AN ANIMAL

(71) Applicant: Advanced Animal Diagnostics, Inc., Morrisville, NC (US)

(72) Inventors: Rodolfo R. Rodriguez, Cary, NC (US); Brian Pike, Durham, NC (US); Ada Tsoi, Morrisville, NC (US); Stefano Bresolin, Garner, NC (US); Jasper N. Pollard, Durham, NC (US); Joy Parr Drach, Pontiac, IL (US); Mitchell Hockett, Raleigh, NC (US); Norah Gerow Bate, Fuquay Varina, NC (US); Danielle Stewart Noel, Raleigh, NC (US); Felipe Guirado Dantas, Sao Jose Do Rio Preto (BR)

(73) Assignee: Advanced Animal Diagnostics, Inc., Morrisville, NC (US)

( * ) Notice: Subject to any disclaimer, the term of this patent is extended or adjusted under 35 U.S.C. 154(b) by 845 days.

(21) Appl. No.: 17/904,742

(22) PCT Filed: Feb. 25, 2021

(86) PCT No.: PCT/US2021/019614
§ 371 (c)(1),
(2) Date: Aug. 22, 2022

(87) PCT Pub. No.: WO2021/173800
PCT Pub. Date: Sep. 2, 2021

(65) Prior Publication Data
US 2023/0115750 A1 Apr. 13, 2023

Related U.S. Application Data

(60) Provisional application No. 62/981,305, filed on Feb. 25, 2020.

(51) Int. Cl.
G01N 33/50 (2006.01)
(52) U.S. Cl.
CPC ..... G01N 33/5091 (2013.01); G01N 2800/52 (2013.01)

(58) Field of Classification Search
None
See application file for complete search history.

(56) References Cited

U.S. PATENT DOCUMENTS

| | | | |
|---|---|---|---|
| 2007/0105105 A1 | 5/2007 | Clelland et al. | |
| 2009/0130702 A1 | 5/2009 | Goldstein | |
| 2010/0162423 A1 | 6/2010 | Denise et al. | |
| 2021/0052511 A1* | 2/2021 | Callahan | A61K 9/0014 |
| 2022/0323401 A1* | 10/2022 | Cooper | A61K 47/34 |

FOREIGN PATENT DOCUMENTS

| | | | |
|---|---|---|---|
| KR | 20010038765 A | 5/2001 | |
| WO | WO-2015188114 A2 * | 12/2015 | G01N 33/80 |
| WO | 2019165064 A1 | 8/2019 | |

OTHER PUBLICATIONS

"International Preliminary Report on Patentability corresponding to International Application No. PCT/US2021/019614 mailed Sep. 9, 2022".
"International Search Report and Written Opinion corresponding to International Application No. PCT/US2021/019614 mailed Jun. 14, 2021".
Wilcox, C. S, et al., "Repeated mixing and isolation: Measuring chronic, intermittent stress in Holstein calves", J. Dairy Sci. 96 :7223-7233 (Jul. 20, 2013).
"Extended European Search Report corresponding to European Application No. 21759626.1 dated Feb. 29, 2024".

* cited by examiner

*Primary Examiner* — Changhwa J Cheu
(74) *Attorney, Agent, or Firm* — Myers Bigel, P.A.

(57) ABSTRACT

The present invention provides a method of identifying and mitigating a risk of deathloss of an animal, comprising receiving, at a processor from a hematology analyzer, information obtained from a sample from said animal, wherein said information comprises a leukocyte absolute count and a leukocyte differential from said sample, said sample comprising leukocytes, analyzing, by said processor, said leukocyte absolute count and said leukocyte differential to determine a survivability index for said animal, and managing the animal based on the survivability index.

29 Claims, 5 Drawing Sheets

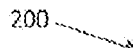
200

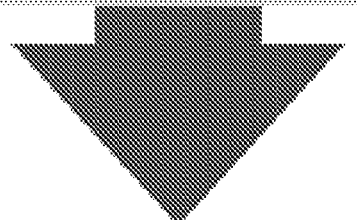

202: Analyze Leukocyte Data

Leukocyte Absolute Count

Neutrophil Absolute Count    Differential of Neutrophils    Maturation Status of Neutrophils Lymphocyte Absolute    Differential of Lymphocytes    Maturation Status of Lymphocytes
Count    Differential of Eosinophils    Maturation Status of Eosinophils Eosinophil Absolute Count    Differential of Basophils    Maturation Status of Basophils Basophil Absolute Count    Differential of Monocytes    Maturation Status of Monocytes Monocyte Absolute Count

204: Evaluate Data with respect to Mathematical Model

206: Assign SI

At Risk of Death    At Risk of Sickness    Low Risk of Sickness or Death

*FIG. 2*

MONTHLY MORTALITY, EXPRESSED AS A PERCENTAGE OF FEEDLOT OCCUPANCY, IN STEERS AND HEIFERS FROM JANUARY 1, 2005 THROUGH DECEMBER 31, 2013
*FIG. 5A*
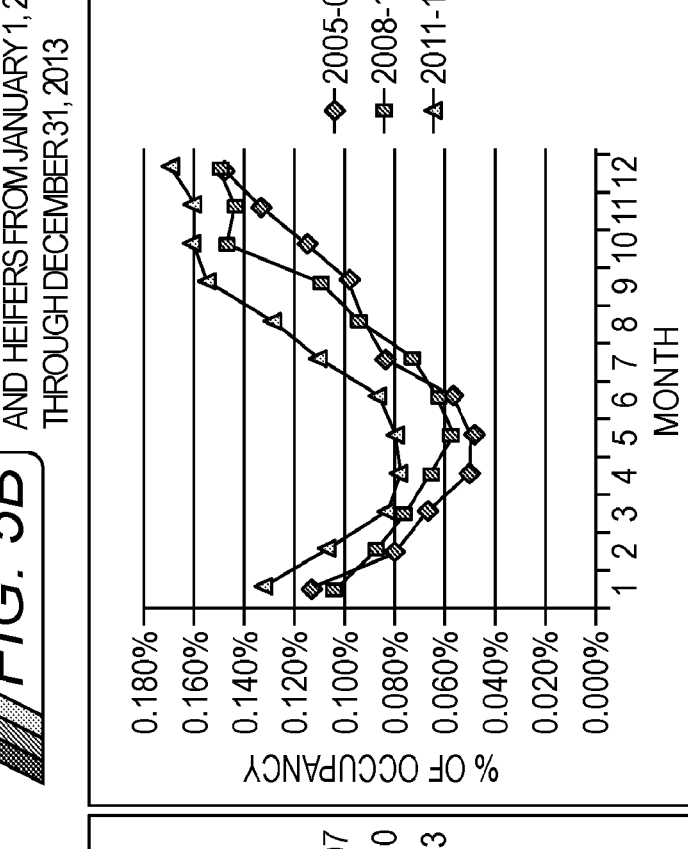
MONTHLY RESPIRATORY MORTALITY, EXPRESSED AS A PERCENTAGE OF FEEDLOT OCCUPANCY, IN STEERS AND HEIFERS FROM JANUARY 1, 2005 THROUGH DECEMBER 31, 2013
*FIG. 5B*
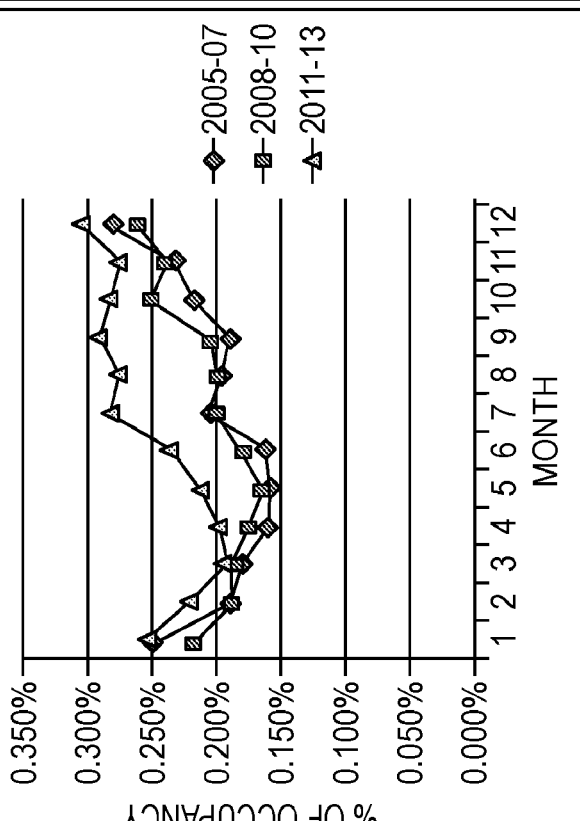
VOGEL ET AL., 2015. A RETROSPECTIVE EVALUATION OF ANIMAL MORTALITY IN US FEEDLOTS: RATE, TIMING, AND CAUSE OF DEATH 49(2):113-123.

METHODS AND COMPOSITIONS FOR IDENTIFYING A SURVIVABILITY INDEX FOR AN ANIMAL

STATEMENT OF PRIORITY

This application is a 35 U.S.C. § 371 national phase application of PCT Application PCT/US2021/019614 filed Feb. 25, 2021, which claims the benefit of U.S. Provisional Application Ser. No. 62/981,305, filed Feb. 25, 2020, the entire contents of each of which are incorporated by reference herein.

BACKGROUND

In the production of livestock such as cattle, swine, farmed fish, and poultry, animal mortality should be managed to conserve resources, keep consumer prices for animal protein as low as possible and enhance the health and wellbeing of the farmed animals. Should sick animals be introduced to a group of animals, infectious disease may spread, which may contribute to increased death loss as well as the use, and potential overuse, of antibiotics. Moreover, sick animals may need special treatment to recover, or some may have an immune system not capable of recovery.

Unfortunately, livestock producers have no objective tools to produce insight into an animal's likelihood of survival or death. Current state of the art in risk evaluation and mitigation includes a practitioner making a subjective assessment of a group of calves, based on such environmental factors as origin, trucking time and distance, pen weight or individual animal weight (this is typically used as a proxy for age since age is typically not available), source of cattle (e.g, sale barn or order buyer vs direct from the cow-calf ranch or backgrounder), and time of year. There is no differentiation between risk of morbidity and risk of mortality. The practitioner will then use this assessment to choose whether to metaphylactically treat the entire pen with antibiotics and may ascribe a subjective estimation of death-loss to the group for financial analysis and planning. At an individual level, there is no way to flag animals likely to die, although practitioners may flag a specific animal for treatment based on visual assessment of clinical signs of illness. This assessment is subjective even when conducted by a highly trained clinician and is further complicated by the prey status of livestock species, which leads many individuals to behaviorally mask early signs of illness. As a result, it is difficult to distinguish sick animals from healthy ones, especially when the assessment must be made for dozens or hundreds of animals in a short period of time. As animals are co-mingled, they become difficult to distinguish and isolate, should they later show signs of illness. Additionally, while application of antibiotics on an individual or group-level can be an effective and easily applied method for protecting both a producer's investment and the welfare of the animals, it is often not enough to prevent death loss. In the fed cattle industry in 2016, 39.3% of large feedlots (>1000 head capacity) and 12.8% of others (<1000 head capacity) treated cattle with an injectable antimicrobial at arrival. See USDA. USDA-*APHIS*-VS-CEAH-NAHMS. Fort Collins, CO. "Antimicrobial Use and Stewardship on U.S. Feedlots, 2017" #751.0419. In spite of this intervention, annual mortality rates in the industry have continued to climb. In one meta-analysis, mortality rates due to bovine respiratory disease were found to have risen by around 30% between 2005 and 2014. See FIGS. 5A and 5B and Vogel et al., 2015.

A retrospective evaluation of animal mortality in US feed-lots: rate, timing, and cause of death. 49(2): 113-123.

Accordingly, techniques to assess survivability would further the ability to manage animals on an industrial scale.

SUMMARY

In one aspect, the present disclosure provides a method of identifying and mitigating a risk of deathloss of an animal, comprising receiving, at a processor from a hematology analyzer, information obtained from a sample from said animal, wherein said information comprises a leukocyte absolute count and a leukocyte differential from said sample, said sample comprising leukocytes, analyzing, by said processor, said leukocyte absolute count and said leukocyte differential to determine a survivability index for said animal, and managing the animal based on the survivability index.

In a further aspect, the present disclosure provides a method of identifying and mitigating a risk of deathloss of an animal, comprising causing said animal to enter a restraining area that is automatically operable, collecting a sample comprising leukocytes from said animal, obtaining a leukocyte absolute count and a leukocyte differential from said sample, analyzing, by a processor, said leukocyte absolute count and said leukocyte differential to determine a survivability index for said animal, and commanding, by said processor, operation of said sorting gate based on said survivability index.

In an additional aspect, the present disclosure provides a method of identifying and mitigating a risk of deathloss of an animal, comprising receiving, at a processor from a hematology analyzer, information obtained from a sample from said animal, wherein said information comprises a leukocyte absolute count and a leukocyte differential from a sample comprising leukocytes, analyzing, by said processor, said leukocyte absolute count and said leukocyte differential to determine a survivability index for said animal, and commanding, by said processor, manual, semi-automatic, or automatic operation of a sorting gate based on said survivability index.

In yet further aspects, the present disclosure provides a method of identifying and mitigating a risk of deathloss of a cohort of animals, comprising receiving, at a processor from a hematology analyzer, information obtained from a first sample from first animal in said cohort of animals and a second sample from a second animal in said cohort of animals, wherein said information comprises a leukocyte absolute count and a leukocyte differential from said first sample and said second sample, said first sample and said second sample comprising leukocytes, analyzing, by said processor, said leukocyte absolute count and said leukocyte differential to determine said survivability index for said cohort of animals, and managing the cohort of animals based on the survivability index.

In another aspect, the present disclosure provides an article of manufacture comprising a non-transitory, machine-readable memory having instructions recorded thereon that, in response to execution by a processor, cause said processor to perform operations comprising receiving, at said processor from a hematology analyzer, information obtained from a sample from an animal, wherein said information comprises a leukocyte absolute count and a leukocyte differential from said sample, and analyzing, by said processor, said leukocyte absolute count and said leukocyte differential to determine a survivability index for said animal.

In yet further aspects, the present disclosure provides a system comprising a processor, a hematology analyzer in communication with said processor, and a tangible, non-transitory memory configured to communicate with said processor, said tangible, non-transitory memory having instructions stored thereon that, in response to execution by said processor, cause said processor to perform operations comprising, receiving, at said processor from said imaging reader, information obtained from a sample from said animal, wherein said information comprises a leukocyte absolute count and a leukocyte differential from said sample, and analyzing, by said processor, said leukocyte absolute count and said leukocyte differential to determine said survivability index for said animal.

BRIEF DESCRIPTION OF THE DRAWINGS

FIG. 2 is a flow diagram of a method in accordance with various embodiments.

FIGS. 5A and 5B are graphs plotting monthly mortality and monthly respiratory mortality, respectively, in accordance with various embodiments.

DETAILED DESCRIPTION

Figure 1:
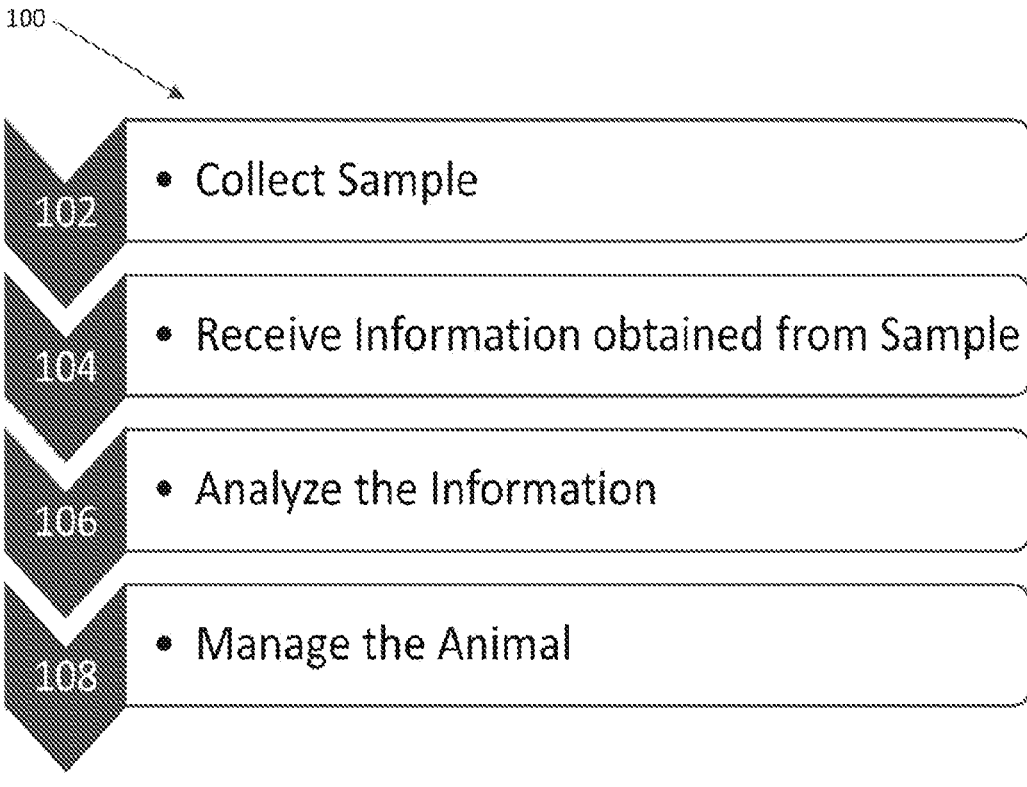
FIG. 1 is a flow diagram of a method in accordance with various embodiments.

The present inventions are now described more fully hereinafter with reference to the accompanying drawings, in which embodiments of the invention are shown. The inventions may, however, be embodied in many different forms and should not be construed as limited to the embodiments set forth herein; rather these embodiments are provided so that this disclosure will be thorough and complete and will fully convey the scope of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

As used in the description of the invention and the appended claims, the singular forms "a," "an" and "the" are intended to include the plural forms as well, unless the context clearly indicates otherwise. For example, "a cell" can mean a single cell or a multiplicity of cells.

Also as used herein, "and/or" refers to and encompasses any and all possible combinations of one or more of the associated listed items, as well as the lack of combinations when interpreted in the alternative ("or").

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

The term "about," as used herein when referring to a measurable value such as an amount or concentration (e.g., the absolute amount of a cell type) and the like, is meant to encompass variations of 10%, 5%, 1%, 0.5%, 0.4% 0.3%, 0.2% or 0.1% of the specified value.

Unless the context indicates otherwise, it is specifically intended that the various features of the invention described herein can be used in any combination. For example, features described in relation to one embodiment may also be applicable to and combinable with other embodiments and aspects of the invention.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention.

All publications, patent applications, patents and other non-patent references mentioned herein are incorporated by reference herein in their entirety.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

As used herein, the term "deathloss," refers to the death of an animal prior to its intended harvesting in a manner such that the resulting carcass is of little to no economic value.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

Various embodiments of the present disclosure provide, among other things, a rapid test that can conveniently be run at key animal movement times (such as at animal intake into a feedlot or other facility) or on a repeated basis to determine a survivability index ("SI") that identifies animals at a risk for mortality above a given threshold, and/or at a risk for mortality above an overall mortality rate of a given cohort of animals. In that regard, the SI provides a rating that categorizes a given animal with respect to risk of mortality without input or interpretation from a trained clinician. In various embodiments, a risk of mortality refers to the probability that an animal will die within a given time period. For example, if an animal is scheduled to be on a feedlot for one month, the risk of mortality may be the risk of the animal dying within the one month time period. The term "rapid" in this context meaning taking place at a rate congruent with maintaining standard speed of commerce for animal processing.

For example, an SI of at risk of death, or risk of morbidity, or sickness (i.e., a sick index), or low risk of mortality or morbidity (i.e., a health index) may be assigned to an animal. An SI of at risk of morbidity due to sickness being in this case indicative of an active viral or bacterial infection, of an immune signature suggestive of suboptimal immune health and/or performance, or of a stress response and its resulting immune suppression. By categorizing an animal into one of these groups, the SI allows for various management strategies to be implemented with respect to the animal to enhance animal welfare and/or the welfare of the cohort of animals collectively. Moreover, improved assessment of risk of death or risk of sickness tends to prevent or reduce the practice of metaphylactic use of antibiotics at arrival to a production facility. Antibiotic use may preserve the health and welfare of animals in the industry, but overuse of these therapies has been shown to increase the prevalence of antimicrobial resistant organisms. Additionally, while antibiotic use is an effective and important tool, it does not prevent all death loss.

Nonlimiting examples of managing the animal based on the survivability index (i.e., management strategies) of this disclosure include moving the animal to a less crowded pen to reduce competition, feeding the animal a special diet, providing supportive therapy to the animal, expedited harvesting of the animal (e.g., within days of determining the survivability index), expedited administering antibiotics to the animal (e.g., while the animal is still restrained to determine the survivability index), providing immunostimulant treatment to the animal, providing individualized treatment to the animal, group treatment and/or segregation. Supportive therapy may comprise the administration of analgesics or nonsteroidal anti-inflammatory drugs (NSAIDs). A special diet may comprise a less dense feed or may include immunostimulants or other additives that support the immune system. By alternative or different management strategy, in some embodiments, it is meant that the management strategy regarding the animal can be changed from a previous management strategy.

Management strategies may also be changed and/or enacted on a group level based on the SI of the individuals in the cohort.

The SI may be calculated based on a variety of data, as described herein. In various embodiments, the SI is calculated based upon one or more of leukocyte absolute count (including absolute counts of total leukocytes, neutrophils, lymphocytes, eosinophils, basophils, and/or monocytes) leukocyte differentials, including differentials of neutrophils, lymphocytes, eosinophils, basophils, and/or monocytes, animal weight, animal sex, animal age, ambient weather conditions, animal body temperature, a transportation time of the animal, animal red blood cell count, animal platelet count, and animal hematocrit. It will be understood that any reference to sex of the animal includes not only distinction between male and female, but also castration status and pregnancy status as applicable. It will additionally be understood that any further reference to neutrophils also encompasses and/or applies to heterophils in avian species.

In various embodiments, various machinery or apparatuses may operate manually, semi-automatically, or automatically in response to an assignment of an SI to a given animal.

In that regard, the assignment of a SI to a given animal may be used to control various machinery or apparatuses to further a management strategy, as disclosed herein. Stated another way, particular machines are operated in accordance with SI assignment to facilitate animal transport, animal care, and/or animal holding.

Animals on which the various embodiments of the present invention may be implemented include, but are not limited to, beef cattle, dairy cattle, sheep, pigs, goats, rabbits, species of farmed fish (e.g., salmon) and poultry (e.g., chickens, turkeys, ducks, geese, quail, pheasant, partridge such as Chukar Partridge, etc.).

While aspects of the present invention are described primarily with respect to beef cattle, embodiments of the present disclosure may also be used in the management of other farm animal industries, such as swine and poultry. For example, the movement of pigs to a nursery, gilt developing unit, breeding herd, or finishing house represents key animal movement times that are similar to that of cattle arriving at the feedlot. Embodiments of the present disclosure can also be useful when animals are re-grouped and moved within the same facility, or at any time the risk to the health of animal is high.

In some embodiments, the methods of the invention do not involve diagnosing mastitis or risk of mastitis in the animal.

Antibiotics or immunostimulants which may be administered to animals in accordance with the present disclosure include, but are not limited to the following antibiotic classes: aminocoumarins, aminoglycosides, amphenicols, cephalosporins, diaminopyrimidines, fluoroquinolones, glycolipids, ionophores, lincosamides, macrolides, penicillins, pleuromutilins, polypeptides, quinoxalines, streptogramins, sulfonamides, tetracyclines and combinations thereof.

Administration of antibiotics may be carried out by any suitable technique, including oral administration (e.g., by including the antibiotic compound in the feed of the animal as a feed additive), parenteral injection (e.g., intravenous injection, subcutaneous injection, intraarterial injection, intramuscular injection, etc.), etc.

In the various embodiments, an animal can be present in a group of animals (e.g., in a herd or flock or school or population, etc.). Each animal can be present singly, or in combination with other animals in the group of animals, in an enclosure, a pen, a corral, a coop, a dwelling, a bam, a field, a pasture, a container, a chute, etc., as would be known in the art.

In various embodiments, one or more (including all) of the steps of the methods of this disclosure can be carried out on site, e.g., at the location where the animal or group of animals may be present, including, for example, chute-side, pen-side, at a sorting gate or sorting device. In various embodiments, the methods of this disclosure can be carried out in an average time of not more than about 120, 90, 60, or 30 seconds. In particular embodiments, the steps are carried out chute-side and/or pen-side and/or at a sorting gate in an average time of not more than about 60 or 30 seconds.

With reference to FIG. 1, method of managing the health of an animal 100 is illustrated. In step 102, information may be obtained from a sample and received, for example by a processor.

In various embodiments a sample from an animal is obtained. The sample, as disclosed herein may include blood, milk, colostrum, urine, nasal mucous, vaginal secretions, mucous secretions, joint fluid, cerebrospinal fluid, fluid from aspirate, fluid from drainage, fluid from lavage or washing, tissue or any other biological sample from an animal that can contain leukocytes. For example, the sample may comprise blood drawn from the animal. In some embodiments of the foregoing, the collecting step is carried out by venipuncture (for example, from the jugular vein or tail vein) or lancing of a capillary bed (for example, in the ear or snout of the animal).

A sample can be collected by any suitable technique with any suitable apparatus, such as a lance, hollow needle, syringe, capillary action chamber, or combination thereof. A device for collecting blood or other samples from cattle or cows is described in PCT Publication No. WO 2017/019743, the disclosure of which is incorporated herein by reference in its entirety. From such initial collection device(s), the unclotted blood (with or without anti-coagulants) can then be transferred to an automated microscope cartridge.

Examples of automated microscope cartridges and automated microscope readers that perform leukocyte differential and absolute cell counts, and which may be adapted to carry out the present disclosure, include those described in U.S. Pat. No. 6,350,613 to Wardlaw, Levine, and Rodriguez, and in US Patent Application Publication No. US 2014/0009596 to Bresolin, Calderwood et al., the disclosures of which are incorporated by reference herein in their entirety. In general, the microscope cartridge includes a bottom portion, an optically transparent top portion (a "cover slip" or "window"), a flat or wedge-shaped chamber therebetween, and a port in fluid communication with that chamber for filling the chamber with a sample. When inserted into the automated microscope, imaging of cells in the sample can be carried out through the "window" or "cover slip," and a leukocyte count and/or differential can be generated automatically from those images.

The sample may be input into an apparatus for immediate analysis. In that regard, the sample may be input into one or more of the apparatuses disclosed herein to obtain information regarding the sample. In various embodiments, immunological information of the animal may be ascertained or otherwise obtained from the sample. Information related to leukocytes, both as an absolute count and as a differential, may be obtained from the sample.

In the methods of this disclosure, a leukocyte absolute count can be, but is not limited to, a leukocyte value in a range from about $X_N \times 10^3$ cells/microliter to about $Y_N \times 10^3$ cells/microliter, wherein $X_N$ is 0, 0.1, 0.2, 0.3, 0.4, 0.5, 0.6, 0.7, 0.8, 0.9, 1.0, 1.1, 1.2, 1.3, 1.4, 1.5, 1.6, or $1.7 \times 10^3$ leukocytes per microliter, and $Y_N$ is 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or $12.0 \times 10^3$ leukocytes per microliter. In the methods of this disclosure, a neutrophil absolute count can be, but is not limited to a neutrophil value in a range from about $X_N \times 10^3$ cells/microliter to about $Y_N \times 10^3$ cells/microliter, wherein $X_N$ is 0, 0.1, 0.2, 0.3, 0.4, 0.5, 0.6, 0.7, 0.8, 0.9, 1.0, 1.1, 1.2, 1.3, 1.4, 1.5, 1.6, or $1.7 \times 10^3$ neutrophils per microliter, and $Y_N$ is 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or $12.0 \times 10^3$ neutrophils per microliter. In the methods of this disclosure, a lymphocyte absolute count can be, but is not limited to, a lymphocyte value in a range from about $X_N \times 10^3$ cells/microliter to about $Y_N \times 10^3$ cells/microliter, wherein $X_N$ is 0, 0.1, 0.2, 0.3, 0.4, 0.5, 0.6, 0.7, 0.8, 0.9, 1.0, 1.1, 1.2, 1.3, 1.4, 1.5, 1.6, or $1.7 \times 10^3$ lymphocytes per microliter, and $Y_N$ is 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or $12.0 \times 10^3$ lymphocytes per microliter. In the methods of this disclosure, an eosinophil absolute count can be, but is not limited to an eosinophil value in a range from about $X_N \times 10^3$ cells/microliter to about $Y_N \times 10^3$ cells/microliter, wherein $X_N$ is 0, 0.1, 0.2, 0.3, 0.4, 0.5, 0.6, 0.7, 0.8, 0.9, 1.0, 1.1, 1.2, 1.3, 1.4, 1.5, 1.6, or $1.7 \times 10^3$ eosinophils per microliter, and $Y_N$ is 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or $12.0 \times 10^3$ eosinophils per microliter. In the methods of this disclosure, a basophil absolute count can be, but is not limited to a basophil value in a range from about $X_N \times 10^3$ cells/microliter to about $Y_N \times 10^3$ cells/microliter, wherein $X_N$ is 0, 0.1, 0.2, 0.3, 0.4, 0.5, 0.6, 0.7, 0.8, 0.9, 1.0, 1.1, 1.2, 1.3, 1.4, 1.5, 1.6, or $1.7 \times 10^3$ basophils per microliter, and $Y_N$ is 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or $12.0 \times 10^3$ basophils per microliter. In the methods of this disclosure, a monocyte absolute count can be, but is not limited to a monocyte value in a range from about $X_N \times 10^3$ cells/microliter to about $Y_N \times 10^3$ cells/microliter, wherein $X_N$ is 0, 0.1, 0.2, 0.3, 0.4, 0.5, 0.6, 0.7, 0.8, 0.9, 1.0, 1.1, 1.2, 1.3, 1.4, 1.5, 1.6, or $1.7 \times 10^3$ monocytes per microliter, and $Y_N$ is 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or $12.0 \times 10^3$ monocytes per microliter. It is understood that the values recited herein include any fraction of one tenth, one hundredth or one thousandth, etc., of said recited values. For example, a range from 0.0 to 0.1 includes 0.01, 0.02, 0.03, 0.04, 0.05, 0.06, 0.07, 0.08 0.09; a range from 1.0 to 1.1 includes 1.01, 1.02, 1.03, 1.04, 1.05, 1.06, 0.07, 1.08, 1.09; and a range from 1.1 to 1.2 includes 1.11, 1.12, 1.13, 1.14, 1.15, 1.16, 1.17, 1.18, 1.19, etc., as if each individual value was explicitly set forth herein.

In various embodiments, a differential of neutrophils, lymphocytes, eosinophils, basophils, and monocytes from a sample may be calculated as a percentage of total cells (e.g., total white blood cells) and/or as a percentage of total blood volume. As used herein, unless noted otherwise, a differential of a leukocyte (e.g., neutrophils, lymphocytes, eosinophils, basophils, and monocytes) refers to the percentage of the leukocyte relative to the total white blood cells.

The differentials for neutrophils, lymphocytes, eosinophils, basophils, and monocytes described herein can be used singly or in any combination in the methods of this disclosure.

A maturation status of one or more of the neutrophils, lymphocytes, eosinophils, basophils, and monocytes from the sample may be obtained from the sample. The maturation status may take a variety of forms, including a percentage of leukocytes that are fully mature relative to the overall number of leukocytes. Maturation status may comprise the percentage of cells at a given stage of maturation relative to the total population of that particular cell type. For example, a myeloblast may develop into a N. promyelocyte, then an N. myelocyte, then an N. metamyelocyte, then an N. band, finally a neutrophil. Maturation status may be, for example, the percentage of one or more of N. promyelocytes, N. myelocytes, N. metamyelocytes, N. bands, and neutrophils to the total amount of N. promyelocytes, N. myelocytes, N. metamyelocytes, N. bands, and neutrophils combined. A myeloblast may develop into an E. promyelocyte, then an E. myelocyte, then an E. metamyelocyte, then an E. band, finally an eosinophil. Maturation status may be, for example, the percentage of one or more of E. myelocytes, E. metamyelocytes, E. bands, and eosinophils to the total amount of E. myelocytes, E. metamyelocytes, E. bands, and eosinophils combined. A myeloblast may develop into a B. promyelocyte, then a B. myelocyte, then a B. metamyelocyte, then a B. band, finally a basophil. Maturation status may be, for example, the percentage of one or more of B. myelocytes, B. metamyelocytes, B. bands, and basophils to the total amount of B. myelocytes, B. metamyelocytes, B. bands, and basophils combined. A myeloblast may develop into a mono-blast, then a promonocyte, finally a monocyte. Maturation status may be, for example, the percentage of one or more of monoblasts, promonocytes, and monocytes to the total amount of monoblasts, promonocytes, and monocytes combined. A lymphoblast may develop into a prolymphocyte, then into a lymphocyte. Maturation status may be, for example, the percentage of one or more of lymphoblasts, prolymphocytes, and lymphocytes to the total amount of lymphoblasts, prolymphocytes, and lymphocytes combined. In various embodiments, maturation status may be percentage of mature monocytes, lymphocytes, eosinophils, basophils, and neutrophils relative to the total number of white blood cells.

In various embodiments, the sample may be analyzed, for example, using apparatuses disclosed here, to obtain animal red blood cell count, animal platelet count, and animal hematocrit. Animal red blood cell count may refer to a number of red blood cells per unit volume found in the sample. Animal platelet count may refer to a number of platelets per unit volume found in the sample. Animal hematocrit may refer to the volume percentage of red blood cells found in the sample.

In accordance with this disclosure, the biological components of the sample, for example, the white blood cells contained in the sample, may be determined by an apparatus comprising: (a) a housing having at least a first interior chamber; (b) an automated microscope in said first interior chamber; (c) at least one first cartridge dispenser in said first interior chamber; (d) at least one first cartridge dispenser access door in said housing and operatively associated with said first cartridge dispenser; (e) at least one first fresh cartridge access port in said housing and operatively associated with said first cartridge dispenser; (f) a filled cartridge insert port in said housing and operatively associated with said automated microscope; and (g) at least one heater operatively associated with said housing configured to heat both said automated microscope and said at least a first cartridge dispenser.

In some embodiments, the apparatus can also comprise (h) a second cartridge dispenser in said first interior chamber; (i) a second cartridge dispenser access door in said housing and operatively associated with said second cartridge dispenser; and (j) a second individual cartridge access port in said housing and operatively associated with said second cartridge dispenser.

In some embodiments, the apparatus can further comprise a heater controller operatively associated with said at least one heater; and at least one temperature sensor in said housing operatively associated with said heater controller.

In further embodiments, a combination apparatus may comprise: (a) a first housing having at least a first interior chamber; (b) an automated microscope in said first interior chamber; (c) a second housing having at least a second interior chamber; (d) at least one first cartridge dispenser in said second interior chamber; (e) at least one first cartridge dispenser access door in said second housing and operatively associated with said first cartridge dispenser; (f) at least a first fresh cartridge access port in said second housing and operatively associated with said first cartridge dispenser; (g) a filled cartridge insert port in said first housing and operatively associated with said automated microscope; and (h) at least one heater operatively associated with each of said first and second housings configured to heat both said automated microscope and said at least a first cartridge dispenser.

In some embodiments, the combination apparatus of this invention can further comprise (i) a second cartridge dispenser in said second interior chamber; (j) a second cartridge dispenser access door in said second housing and operatively associated with said second cartridge dispenser; and (k) a second individual cartridge access port in said second housing and operatively associated with said second cartridge dispenser.

In an additional embodiment, the combination apparatus can also further comprise a heater controller operatively associated with each of said at least one heater; and at least one temperature sensor in each of said housings and operatively associated with said heater controller.

In various embodiments, an imaging reader is housed in or associated with the apparatus and configured to optically evaluate the sample. The imaging reader includes a camera or other optical sensor, a controller or other processor, and a display. The camera is configured to image the sample, which may be inserted into the imaging reader, for example, using a sample cartridge. The camera may include any optical components for imaging the sample, including a light source, lenses, and the like. The camera may be any suitable imaging device, such as a CCD/CMOS device, and may detect and produce digital images and/or intensity values of various signals. The imaging reader may be an automated microscope apparatus.

Individual components of the imaging reader described herein may be as known in the art, or variations thereof that will be apparent to those skilled in the art based on the instant disclosure and prior automated microscopy apparatus such as described in U.S. Pat. No. 4,998,284 to Bacus; U.S. Pat. No. 5,790,710 to Price; U.S. Pat. No. 6,381,058 to Ramm; U.S. Pat. No. 6,929,953 to Wardlaw; U.S. Pat. No. 6,927,903 to Stuckey; U.S. Pat. No. 8,000,511 to Perz; U.S. Pat. No. 8,045,165 to Wardlaw; U.S. Pat. No. 8,081,303 to Levine; US Patent Application Nos. 2001/0041347 to Sammak; or 2009/0233329 to Rodriguez. The imaging reader may be a QSCOUT™ reader commercially available from Advanced Animal Diagnostics (Morrisville, North Carolina, USA).

It will be understood that the methods of this invention can be carried out with the apparatus and/or with the combination apparatus.

In step 104, the information obtained from the sample is analyzed, for example, by the processor. In various embodiments, the leukocyte absolute count and the leukocyte differential may be used to determine the SI.

With brief reference to FIG. 2, step 106 is illustrated in additional detail. In step 202, one or more of the total leukocyte absolute count, neutrophil absolute count, the lymphocyte absolute count, the eosinophil absolute count, the basophil absolute count, the monocyte absolute count, the neutrophil differential, the lymphocyte differential, the eosinophil differential, the basophil differential, the monocyte differential, and the maturation status of one or more of the neutrophils, lymphocytes, eosinophils, basophils, and monocytes from the sample is analyzed and may be used to base the assignment of the SI. The analysis may comprise determining relationships relative to one another and/or relative to predetermined values associated with healthy animals.

In step 204, the processor determines whether one or more of the measurements yielded by the sample analysis exceeds a predetermined threshold as defined by a mathematical model to include, but not limited to decision tree, logistic regression, or machine learning modeling. Based on the analysis an SI may be assigned to an animal.

For example, in step 204, the processor determines whether the lymphocyte absolute count or differential is above a lymphocyte threshold to obtain a high lymphocyte rating. The ceiling lymphocyte threshold may represent the expected upper limit of lymphocyte absolute count or differential for the animal. In that regard, the lymphocyte absolute count or differential may be regarded as high. In various embodiments, in step 204, the processor determines whether the lymphocyte absolute count or differential is below a floor lymphocyte threshold to obtain a low lymphocyte rating. The floor lymphocyte threshold may represent the expected lower limit of lymphocyte absolute count or differential for the animal. In that regard, the lymphocyte absolute count or differential may be regarded as low. Also, in step 204, the processor determines whether the neutrophil absolute count or differential is above a ceiling neutrophil threshold to obtain a high neutrophil rating. The ceiling neutrophil threshold may represent the expected upper limit of neutrophil absolute count or differential for the animal. In that regard, the neutrophil absolute count or differential may be regarded as high. In various embodiments, in step 204, the processor determines whether the neutrophil absolute count or differential is below a floor neutrophil threshold to obtain a low neutrophil rating. The floor neutrophil threshold may represent the expected lower limit of neutrophil absolute count or differential for the animal. In that regard, the neutrophil absolute count or differential may be regarded as low. In various embodiments, in step 204, the processor determines whether the basophil absolute count or differential is below a floor basophil threshold to obtain a low basophil rating. In various embodiments, in step 204, the processor determines whether the basophil absolute count or differential is above a ceiling basophil threshold to obtain a high basophil rating. The ceiling basophil threshold may represent the expected upper limit of basophil absolute count or differential for the animal. In that regard, the basophil absolute count or differential may be regarded as high. The floor basophil threshold may represent the expected lower limit of basophil absolute count or differential for the animal. In that regard, the basophil absolute count or differential may be regarded as low.

In various embodiments, in step 204, the processor determines whether the total leukocyte absolute count is above a ceiling total leukocyte threshold to obtain a high total leukocyte rating. The ceiling total leukocyte threshold may represent the expected upper limit of total leukocyte absolute count for the animal. In that regard, the total leukocyte absolute count may be regarded as high. The floor total leukocyte threshold may represent the expected lower limit of total leukocyte absolute count for the animal. In that regard, the total leukocyte absolute count may be regarded as low.

In various embodiments, in step 204, the processor determines whether the eosinophil absolute count is above a ceiling eosinophil threshold to obtain a high eosinophil rating. The ceiling eosinophil threshold may represent the expected upper limit of eosinophil absolute count for the animal. In that regard, the total eosinophil absolute count may be regarded as high. The floor eosinophil threshold may represent the expected lower limit of eosinophil absolute count for the animal. In that regard, the eosinophil absolute count may be regarded as low. In step 206 based on this analysis an SI is assigned to the animal. For example, an SI index of at risk of death may be assigned in part based on at least one of the high lymphocyte rating, the low lymphocyte rating, the high neutrophil rating, the low neutrophil rating, the high basophil rating, the low basophil rating, the high total leukocyte rating and the low total leukocyte rating.

With reference back to FIG. 1, step 106 includes managing the animal based upon the SI. In that regard, a management strategy may be implemented based upon the SI. Nonlimiting examples of a managing the animal based on the survivability index of this disclosure include moving the animal to a less crowded pen to reduce competition, feeding the animal a special diet, providing supportive therapy to the animal, expedited harvesting of the animal, expedited administering of antibiotics to the animal, providing immunostimulant treatment to the animal, providing individualized treatment to the animal, group treatment and/or segregation. By alternative or different management strategy, in some embodiments, it is meant that the management strategy regarding the animal can be changed from a previous management strategy.

Figure 4:
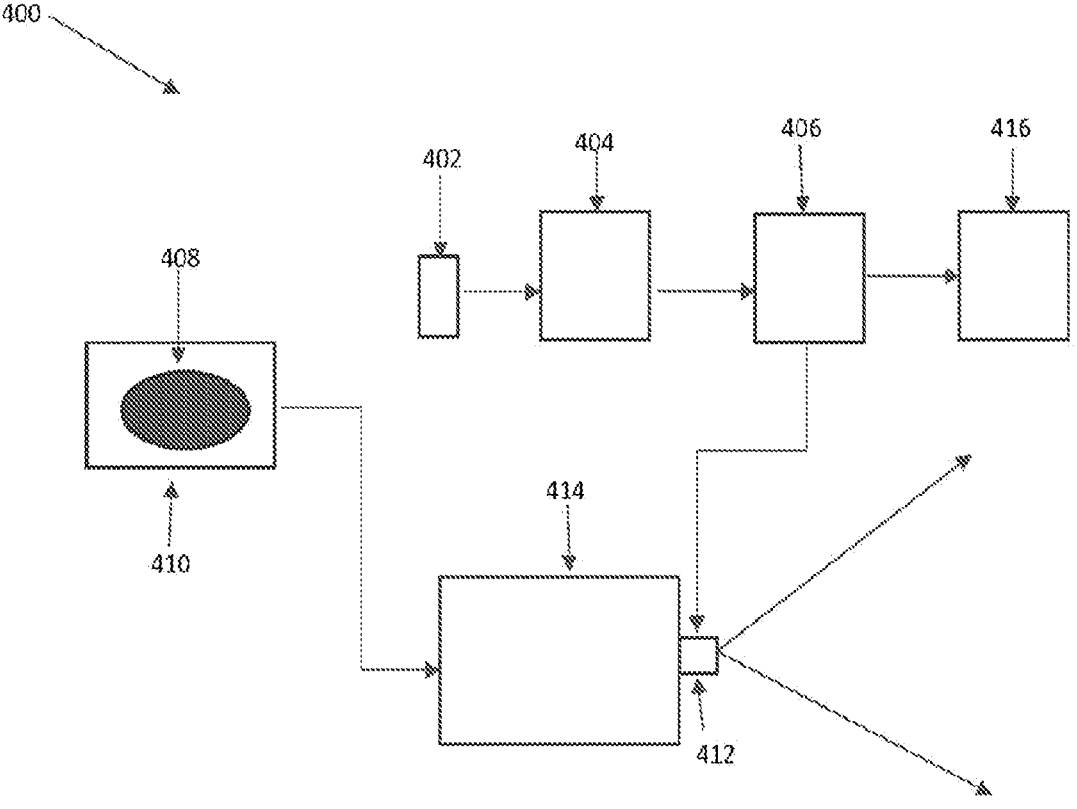
FIG. 4 is a schematic diagram of a system in accordance with various embodiments.

With reference to FIGS. 1 and 4, a system for managing the health of an animal 400 is illustrated. Sample 402 is taken from animal 408. Sample 402 may be any sample as described herein, for example, a blood sample. Animal 408 is restrained in a restraining area such as restraining area 410. Restraining area 410 comprises a mechanical restraint that prevents animal 408 from moving beyond restraining area 410. Sorting gate 414 comprises a mechanical barrier which will selectively release animal 408 in the direction of a specific pen or enclosure according to the SI assignment. Sorting gate 414 may further comprise electromechanical actuation device 412. Electromechanical actuation device 412 can comprise electromechanical actuators, solenoids, servomotors, motor-driven hydraulic pistons, or other mechanical devices for actuating the sorting gate 414. Electromechanical actuation device 412 can also comprise an electronic interface configured to be in electronic communication with a controller or processor and to command the electromechanical actuation device 412 in accordance with the commands from the controller or processor.

Sample 402 is read by hematology analyzer (e.g., imaging reader) 404, as described herein. The imaging reader 404 includes a camera, a processor 406, and a display 416. As illustrated, the camera is configured to image the sample 402, which may be inserted into the imaging reader 404, for example, using a sample cartridge. The camera may include any optical components for imaging the sample, including a light source, lenses, and the like. The camera may be any suitable imaging device, such as a CCD/CMOS device, and may detect and produce digital images and/or intensity values of various signals. The imaging reader 404 may be an automated microscope apparatus.

Individual components of the imaging reader 404 described herein may be as known in the art, or variations thereof that will be apparent to those skilled in the art. The processor 406 and may be configured to receive intensity values and/or images from the camera and to analyze the intensity values and/or images and to display the results on a display 416.

The processor 406 may be further configured to carry out various automated steps of the methods described herein. Display 416 may be an LCD, CRT, OLED or other display type capable of displaying information. In various embodiments, display 416 displays an indicator representative of the assigned SI. Such indicator may be a color code, icon, graphic, or language.

A nonlimiting example of an apparatus of this invention is the QSCOUT© reader, which passes an optical signal through a focal lens and then through a emission filter and then to a monochrome camera. Images are processed for signal intensity from the camera to the processor 406. Results are then displayed on the display device, which in this case is a color touchscreen. Results may additionally be transmitted to a cloud-based data storage system when internet access is available for record keeping and animal- or operation-level data analysis.

In that regard, imaging reader 404 may obtain one or more of a leukocyte absolute count, a leukocyte differential, a neutrophil absolute count, a lymphocyte absolute count, an eosinophil absolute count, a basophil absolute count, and a monocyte absolute count from said sample, a neutrophil differential, a lymphocyte differential, an eosinophil differential, a basophil differential, a monocyte differential, a maturation status of leukocytes, maturation status of neutrophils, maturation status of eosinophils, maturation status of basophils, maturation status of lymphocytes, and a maturation status of monocytes. Imaging reader 404 passes this information to processor 406, which may be contained within the same physical housing as imaging reader 404 or may be disposed remotely to imaging reader 404, such an in a cloud computing deployment. Stated another way, processor 406 receives the information obtained from the sample as in step 104 and, in various embodiments, may transmit the information to a cloud computing system.

Processor 406 performs the step 106 by analyzing the information received from the imaging reader 404 as well as other information it may have received from other sources, including one or more of a sex of animal 408, a weight of animal 408, an age of animal 408, an ambient temperature, a relative humidity, a transportation time of animal 408, and a body temperature of animal 408.

Processor 406 may then assign a SI to animal 408. Processor 406 may be in electronic communication with sorting gate 414, in particular, with electromechanical actuation device 412. After assignment of an SI, processor 406 commands sorting gate 414 by sending a command to electromechanical actuation device 412 to automatically operate in response to the assignment of an SI and in accordance with the SI. Stated another way, processor 406 may automatically actuate sorting gate 414 in accordance with the SI, allowing the processor to control the sorting gate 414 to selectively release the animal into a pen or enclosure associated with the assigned SI index.

In various embodiments, after assignment of an SI, processor 406 may command the display of the SI indicator on display 416. In response, sorting gate 414 may be manually operated in according with the SI, selectively releasing the animal into a pen or enclosure associate with the assigned SI index.

Figure 3:
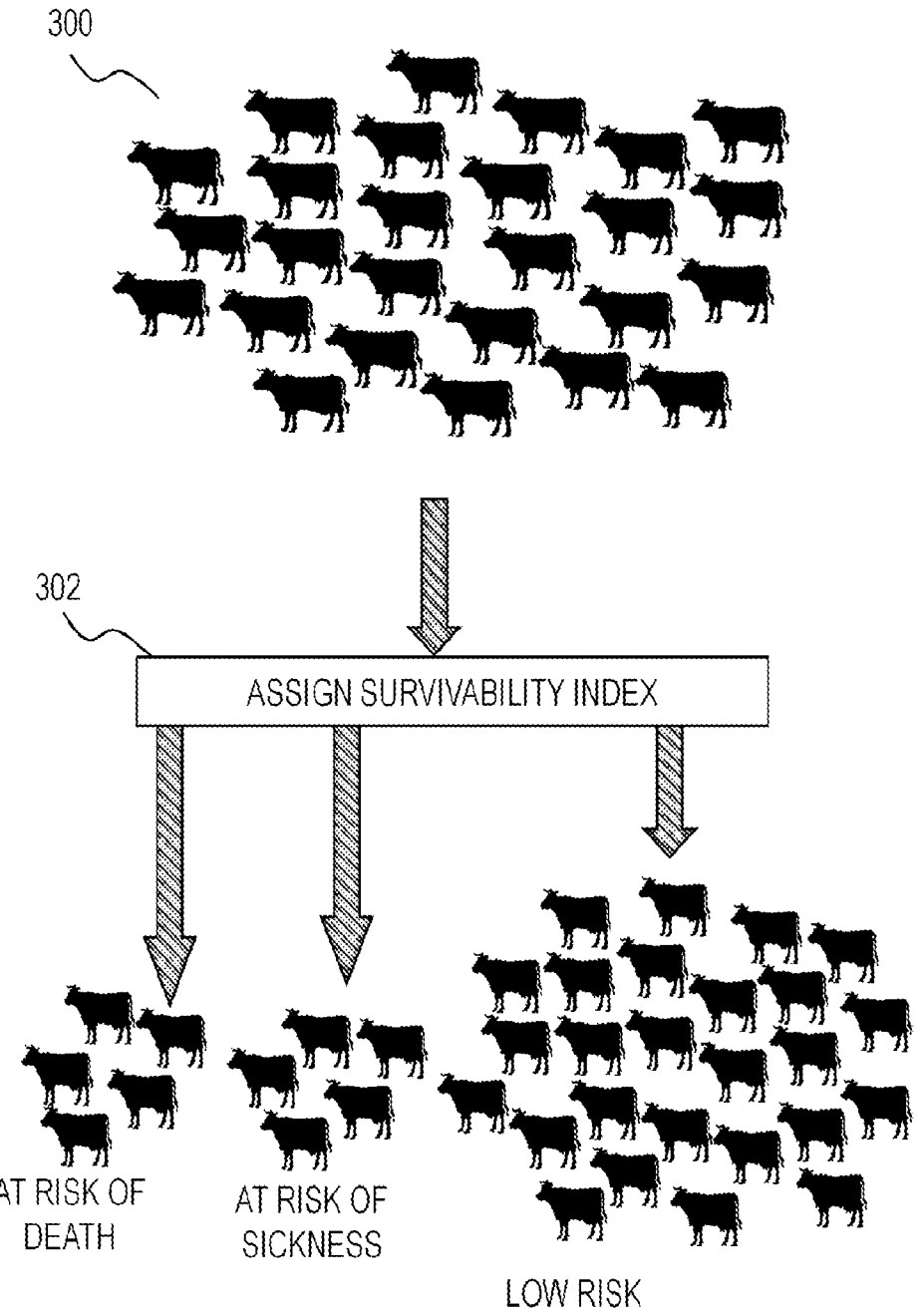
FIG. 3 is a schematic diagram of assignment of a survivability index in accordance with various embodiments.

With additional reference to FIG. 3 and continued reference to FIG. 4, for example, at step 302 of assigning a SI, processor 406 may command sorting gate 414 to release an animal with an SI of at risk of death to a first cohort, and animal with an SI risk of sickness into a second cohort, and an animal with a low risk of death to a third cohort.

With reference back to FIG. 1, in various embodiments, method 100 may be performed iteratively across many animals individually, for example, in connection with beef or dairy cattle. However, particularly where the animals under study are small, it may be more efficient to perform method 100 iteratively upon two or more animals in a cohort of animals. For example, a first sample may be taken from a first animal in the cohort of animals and second sample may be taken from a second animal in the cohort of animals. The samples may be analyzed separately, and an SI index derived from both the first sample and the second sample may be assigned to all animals in the cohort of animals. In various embodiments, the samples may be combined into a pooled sample and then analyzed. In this manner, an SI index may be derived from the pooled sample and the SI index may be assigned to all animals in the cohort of animals.

The present disclosure is explained in greater detail in the following non-limiting Examples.

EXAMPLE

Blood is collected from beef cattle chute side from the jugular vein, ear vein, tail vein, etc using any suitable blood collection and transfer device. From the collection and transfer device, the blood is transferred into an automated microscope cartridge. The cartridge has one microfluidic chamber, with a 9 mm×18 mm optically transparent cover slip. There are other geometries that can accomplish this, such as (i) a coverslip that is 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13, 3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18, 18.1 mm in one side and in any combination in the same plane such that the other side can be 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13, 3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18, 18.1 mm; (ii) at a depth of 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13, 3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9 or 20.0 microns deep; (iii) may not have straight and orthogonal sides (e.g. a molded contoured edge); (iv) may not be parallel and thus may have an angle of 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 degrees (v) will have a known volume range of the sample area (i.e., its viewing area multiplied by its depth).

A suitable automated microscope is an AAD QScout automated microscope/leukocyte reader (available from Advanced Animal Diagnostics, Inc. (Morrisville, NC USA) modified as described above to contain a thermally protected storage area for fresh cartridges, and to keep the automated microscope itself at substantially the same temperature as those fresh cartridges. In general, it is important in chemistry and biological applications to keep the device and the cartridge at a minimum of 70° F., and preferably closer to 90° F. Since the unit is typically operated outside and exposed to very cold temperatures on the feedlot, this thermal protection is important to prevent thermal "shock" of the white blood cells that may occur in colder ambient temperatures and impede successful stain penetration when the sample is added to the fresh slide.

Furthermore, keeping the fresh cartridges and instrument at substantially the same temperature reduces the effect of coefficient of thermal expansion mismatch (CTE mismatch). The cartridge is typically made of multiple materials, and contains a space or void into which fresh sample fills. Any CTE mismatch can cause slight warping which can lead to cells drifting out of the focal plane of the automated microscope. Maintaining uniform temperatures reduces this effect, allowing for fewer focal points and decreasing overall time to result. Otherwise, the operator would have to continually refocus to maintain focal plane as the slide expands and contracts.

The AAD QScout reader can produce the following results from a sample (e.g., a blood sample): (1) total leukocyte count per microliter; (2) total lymphocyte count per microliter; (3) total neutrophil count per microliter; (4) total eosinophil count per microliter; (5) total monocyte count per microliter; (6) percent neutrophil, percent eosinophil, percent lymphocyte, percent monocyte, and percent basophil; and (7) detection of immature, non-segmented neutrophils including band neutrophils. Additionally, other variants may optionally be included, such as ratios of the above blood cell types, combination of cell types and ratios of combinations of cell types, total leukocyte count, body temperature, and/or red blood cell count, optionally in combination with the animals' sex, weight, age and body temperature.

A study of SI was conducted on a cohort of 507 cattle. The collection procedure proceeded according substantially to those disclosed herein as each head of cattle was admitted to a feedlot. Each of the 507 cattle were assigned a SI of either low risk of death or sickness, at risk of death or sickness from Bovine Respiratory Disease (BRD), and at risk of death. The cohort had a mortality of 17.2%. In that regard, without application of alternate management strategies, the cohort would likely have seen approximately 17.2% of the cohort die prior to the end of each animal's time in the feedlot.

Thirty-nine (39) of the cattle had an SI of at risk of death. Each of these had a mortality of 51.3%. The remaining four hundred and sixty-eight (468) of the cattle had an SI of low risk of death or sickness or at risk of sickness. Each of these had a mortality of 14.3%. In that regard, the assignment of SI to each animal allows for identification of cattle most at risk for mortality, in this example, nearly four times the mortality of the overall cohort.

In that regard, by implementing management strategies in response to the at risk of death group, animals may be given additional care to recuperate or may be harvested to end potential animal pain and suffering.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. As those skilled in the art will appreciate, user computer may include an operating system (e.g., WINDOWS®, OS2, UNIX®, LINUX®, SOLARIS®, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations or any of the operations may be conducted or enhanced by artificial intelligence (AI) or machine learning. Artificial intelligence may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit. Various embodiments include a display device configured to display the SI by displaying one or more indicators. The one of more indicators may be color coded, written in a human language, or encoded in a machine readable language.

As will be appreciated by one of ordinary skill in the art, the system or any of its components may be embodied as a customization of an existing system, an add-on product, a processing apparatus executing upgraded software, a standalone system, a distributed system, a method, a data processing system, a device for data processing, and/or a computer program product. Accordingly, any portion of the system or a module may take the form of a processing apparatus executing code, an internet-based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general-purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS®, webpages, websites, web forms, prompts, etc. Practitioners will appreciate that the illustrated steps described herein may comprise in any number of configurations including the use of WINDOWS®, webpages, web forms, popup WINDOWS®, prompts and the like. It should be further appreciated that the multiple steps as illustrated and described may be combined into single webpages and/or WINDOWS® but have been expanded for the sake of simplicity. In other cases, steps illustrated and described as single process steps may be separated into multiple webpages and/or WINDOWS® but have been combined for simplicity.

As used herein, "electronic communication" may comprise a physical coupling and/or non-physical coupling capable of enabling system components to transmit and receive data. For example, "electronic communication" may refer to a wired or wireless protocol such as a CAN bus protocol, an Ethernet physical layer protocol (e.g., those using TOBASE-T, 100BASE-T, 1000BASE-T, etc.), an IEEE 1394 interface (e.g., FireWire), Integrated Services for Digital Network (ISDN), a digital subscriber line (DSL), an 802.11a/b/g/n/ac signal (e.g., Wi-Fi), a wireless communications protocol using short wavelength UHF radio waves and defined at least in part by IEEE 802.15.1 (e.g., the BLUETOOTH© protocol maintained by Bluetooth Special Interest Group), a wireless communications protocol defined at least in part by IEEE 802.15.4 (e.g., the ZIGBEE® protocol maintained by the ZigBee alliance), a cellular protocol, an infrared protocol, an optical protocol, or any other protocol capable of transmitting information via a wired or wireless connection. The processor, sorting gate, display device, and other components disclosed herein may be in electronic communication with one another.

As used herein, "transmit" may include sending electronic data from one system component to another over a network connection. Additionally, as used herein, "data" or "information" may include encompassing information such as commands, queries, files, data for storage, and the like in digital or any other form.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The foregoing is illustrative of the present invention, and is not to be construed as limiting thereof. The invention is defined by the following claims, with equivalents of the claims to be included therein.

The invention claimed is:

1. A method of identifying and mitigating a risk of deathloss of an animal, comprising:
   (a) receiving, at a processor from a hematology analyzer, information obtained from a sample from said animal, wherein said information comprises a leukocyte absolute count, a leukocyte differential, and a maturation status for one or more of neutrophils, lymphocytes, eosinophils, basophils, and monocytes from said sample, said sample comprising leukocytes;
   (b) analyzing, by said processor, said leukocyte absolute count, said leukocyte differential, and said maturation status for one or more of neutrophils, lymphocytes, eosinophils, basophils, and monocytes to determine a survivability index for said animal; and
   (c) managing the animal based on said survivability index, wherein said managing the animal comprises one or more of:
   moving said animal to a less crowded pen to reduce competition;
   feeding said animal a special diet;
   providing supportive therapy selected from administering analgesics or nonsteroidal anti-inflammatory drugs (NSAIDs) to said animal;
   expedited harvesting of said animal; and
   expedited administration of antibiotics to said animal.

2. A method of identifying and mitigating a risk of deathloss of an animal, comprising:
   (a) causing said animal to enter a sorting gate that is automatically operable;
   (b) collecting a sample comprising leukocytes from said animal;
   (c) obtaining a leukocyte absolute count, a leukocyte differential, and a maturation status for one or more of neutrophils, lymphocytes, eosinophils, basophils, and monocytes from said sample;
   (d) analyzing, by a processor, said leukocyte absolute count, said leukocyte differential, and said maturation status for one or more of neutrophils, lymphocytes, eosinophils, basophils, and monocytes to determine a survivability index for said animal; and
   (e) commanding, by said processor, operation of said sorting gate based on said survivability index thereby sorting said animal based on said survivability index.

3. The method of claim 2, further comprising commanding, by said processor, a display device to display an indicator to indicate said survivability index.

4. The method of claim 2, wherein (c) further comprises obtaining one or more of a neutrophil absolute count, a lymphocyte absolute count, an eosinophil absolute count, a basophil absolute count, and a monocyte absolute count from said sample.

5. The method of claim 2, wherein said sample comprises blood taken from said animal.

6. The method of claim 2, wherein (c) further comprises obtaining each of a neutrophil absolute count, a lymphocyte absolute count, an eosinophil absolute count, a basophil absolute count, and a monocyte absolute count from said sample.

7. The method of claim 2, wherein (c) further comprises obtaining a differential of one or more of neutrophils, lymphocytes, eosinophils, and monocytes from said sample.

8. The method of claim 2, wherein (c) further comprises obtaining a maturation status for each of neutrophils, lymphocytes, eosinophils, and monocytes in said sample.

9. The method of claim 2, wherein (c) further comprises obtaining at least one of a sex of said animal, a castration status of said animal, a weight of said animal, an age of said animal, a transportation time of said animal, a relative humidity, and a body temperature of said animal.

10. The method of claim 2, wherein (c) further comprises obtaining at least one of a red blood cell count, a platelet count, and a hematocrit level from said sample.

11. The method of claim 4, wherein (d) further comprises:
   determining, by said processor, whether said lymphocyte absolute count or differential is above a lymphocyte threshold to obtain a high lymphocyte rating,
   determining, by said processor, whether said neutrophil absolute count or differential is above a ceiling neutrophil threshold to obtain a high neutrophil rating,
   determining, by said processor, whether said neutrophil absolute count or differential is below a floor neutrophil threshold to obtain a low neutrophil rating,
   determining, by said processor, whether said lymphocyte absolute count or differential is below a floor lymphocyte threshold to obtain a low lymphocyte rating,
   determining, by said processor, whether said eosinophil absolute count or differential is above a ceiling eosinophil threshold to obtain a high eosinophil rating, and/or
   determining, by said processor, whether said eosinophil absolute count or differential is below a floor eosinophil threshold to obtain a low eosinophil rating.

12. The method of claim 11, wherein (d) further comprises assigning, by said processor, a survivability index to said animal based upon at least one of a total leukocyte count neutrophil absolute count, lymphocyte absolute count, eosinophil absolute count, basophil absolute count, and monocyte absolute count.

13. The method of claim 11, wherein (d) further comprises:
   assigning, by said processor, a survivability index of risk of death to said animal based upon obtaining at least one of said high lymphocyte rating, said high neutrophil rating, said high eosinophil rating, said low neutrophil rating, and said low lymphocyte rating,
   assigning, by said processor, a survivability index of risk of morbidity due to sickness to said animal based upon obtaining at least one of said high lymphocyte absolute count rating, said high neutrophil absolute count rating, and said low neutrophil absolute count rating,
   assigning, by said processor, a survivability index of a low risk of mortality or morbidity to said animal based upon obtaining none of said high lymphocyte absolute count rating, said high neutrophil absolute count rating, and said low neutrophil absolute count rating.

14. The method of claim 2, wherein (e) further comprises commanding, by said processor, operation of said sorting gate to open into a holding pen in response to assignment of said survivability index of risk of death.

15. The method of claim 2, wherein (e) further comprises commanding, by said processor, operation of said sorting gate to open into a hospital or convalescent pen in response to assignment of said survivability index of risk of morbidity due to sickness.

16. The method of claim 12, wherein (e) further comprises commanding, by said processor, operation of said sorting gate to open into a general population pen in response to assignment of said survivability index of low risk of mortality or morbidity.

17. The method of claim 1, further comprising performing financial analysis based on the survivability index.

18. The method of claim 2, further comprising performing financial analysis based on the survivability index.

19. The method of claim 1, further comprising commanding, by said processor, a display device to display an indicator to indicate said survivability index.

20. The method of claim 1, wherein said information further comprises one or more of a neutrophil absolute count, a lymphocyte absolute count, an eosinophil absolute count, a basophil absolute count, and a monocyte absolute count from said sample.

21. The method of claim 1, wherein said sample comprises blood taken from said animal.

22. The method of claim 1, wherein said information further comprises each of a neutrophil absolute count, a lymphocyte absolute count, an eosinophil absolute count, a basophil absolute count, and a monocyte absolute count from said sample.

23. The method of claim 1, wherein said information further comprises a differential of one or more of neutrophils, lymphocytes, eosinophils, and monocytes from said sample.

24. The method of claim 1, wherein said information further comprises obtaining a maturation status for each of neutrophils, lymphocytes, eosinophils, and monocytes in said sample.

25. The method of claim 1, wherein said information further comprises at least one of a sex of said animal, a castration status of said animal, a weight of said animal, an age of said animal, a transportation time of said animal, a relative humidity, and a body temperature of said animal.

26. The method of claim 1, wherein said information further comprises at least one of a red blood cell count, a platelet count, and a hematocrit level from said sample.

27. The method of claim 20, wherein (b) further comprises:

determining, by said processor, whether said lymphocyte absolute count or differential is above a lymphocyte threshold to obtain a high lymphocyte rating, determining, by said processor, whether said neutrophil absolute count or differential is above a ceiling neutrophil threshold to obtain a high neutrophil rating, determining, by said processor, whether said neutrophil absolute count or differential is below a floor neutrophil threshold to obtain a low neutrophil rating, determining, by said processor, whether said lymphocyte absolute count or differential is below a floor lymphocyte threshold to obtain a low lymphocyte rating, determining, by said processor, whether said eosinophil absolute count or differential is above a ceiling eosinophil threshold to obtain a high eosinophil rating, and/or determining, by said processor, whether said eosinophil absolute count or differential is below a floor eosinophil threshold to obtain a low eosinophil rating.

28. The method of claim 20, wherein (b) further comprises assigning, by said processor, a survivability index to said animal based upon at least one of a total leukocyte count, neutrophil absolute count, lymphocyte absolute count, eosinophil absolute count, basophil absolute count, and monocyte absolute count.

29. The method of claim 27, wherein (b) further comprises:

assigning, by said processor, a survivability index of risk of death to said animal based upon obtaining at least one of said high lymphocyte rating, said high neutrophil rating, said high eosinophil rating, said low neutrophil rating, and said low lymphocyte rating, assigning, by said processor, a survivability index of risk of morbidity due to sickness to said animal based upon obtaining at least one of said high lymphocyte absolute count rating, said high neutrophil absolute count rating, and said low neutrophil absolute count rating, assigning, by said processor, a survivability index of a low risk of mortality or morbidity to said animal based upon obtaining none of said high lymphocyte absolute count rating, said high neutrophil absolute count rating, and said low neutrophil absolute count rating.

* * * * *